US008043236B2

(12) United States Patent
Goldshtein et al.

(10) Patent No.: US 8,043,236 B2
(45) Date of Patent: Oct. 25, 2011

(54) BREATH TRAINING DEVICE

(75) Inventors: Yakov Abrammerovich Goldshtein, Moscow (RU); Boris Aronovich Dyshko, Moscow (RU); Alexandr Ivanovich Kashirin, Moscow (RU); Alexandr Borisovich Kochergin, Penza (RU); Igor Vladimirovich Panteleev, Moscow (RU)

(73) Assignee: OOO "Sport Technology", Moscow (RU)

( * ) Notice: Subject to any disclaimer, the term of this patent is extended or adjusted under 35 U.S.C. 154(b) by 849 days.

(21) Appl. No.: 12/054,590

(22) Filed: Mar. 25, 2008

(65) Prior Publication Data

US 2008/0228113 A1 Sep. 18, 2008

Related U.S. Application Data

(63) Continuation of application No. PCT/RU2007/000008, filed on Jan. 12, 2007.

(30) Foreign Application Priority Data

Jan. 24, 2006 (RU) ................................ 2006101896

(51) Int. Cl.
*A63B 23/18* (2006.01)
*A61M 16/00* (2006.01)

(52) U.S. Cl. ... 601/41; 482/13; 128/200.24; 128/205.24

(58) Field of Classification Search .............. 601/41–44; 128/200.24, 204.18, 204.24, 204.26, 205.24, 128/205.25, 206.21, 206.29, 207.11, 207.16; 482/13

See application file for complete search history.

(56) References Cited

U.S. PATENT DOCUMENTS

| | | | | |
|---|---|---|---|---|
| 5,165,393 | A | 11/1992 | Kawaguchi | |
| 5,451,190 | A * | 9/1995 | Liardet | 482/13 |
| 5,890,998 | A * | 4/1999 | Hougen | 482/13 |
| 5,910,071 | A * | 6/1999 | Hougen | 482/13 |
| 7,779,841 | B2 * | 8/2010 | Dunsmore et al. | 128/205.24 |

FOREIGN PATENT DOCUMENTS

| | | | |
|---|---|---|---|
| RU | 1801469 | A1 | 3/1993 |
| RU | 2 147 906 | C1 | 4/2000 |
| SU | 1766369 | A1 | 10/1992 |

OTHER PUBLICATIONS

International Search Report from International Application No. PCT/RU2007/000008, filed Jan. 12, 2007, mailed on May 24, 2007.

* cited by examiner

*Primary Examiner* — Quang D Thanh
(74) *Attorney, Agent, or Firm* — Houston Eliseeva, LLP

(57) ABSTRACT

The inventive breath training device comprises a respiratory tube, a low-frequency mechanical air oscillation generator provided with an oscillation chamber embodied therein and provided with an input channel which is embodied in the form of an upwardly extending saddle-shaped body of revolution, contains a spherical ball and is connected to the respiratory tube and to an output channel communicating with ambient air, wherein the respiratory tube is provided with a jacket in which the body of the low-frequency mechanical air oscillation generator rotatable about a horizontal axis is fixed and a bypass chamber provided with an inspiratory tube is formed, said inspiratory tube comprises an inspiratory valve provided with a tubular attachment and the output channel of the oscillation chamber of the low-frequency mechanical air oscillation generator is also provided with an expiratory valve.

2 Claims, 2 Drawing Sheets

BREATH TRAINING DEVICE

RELATED APPLICATIONS

This application is a Continuation of International Application Number PCT/RU2007/000008, filed on Jan. 12, 2007, which claims priority to Russian Patent Application No. RU 2006101896, filed on Jan. 24, 2006, both of which are incorporated herein by reference in their entirety.

FIELD OF THE INVENTION

This invention relates to the devices that achieve respiratory training by providing additional resistance to the exhaled airflow; the invention's purpose is to increase efficiency of the training process.

BACKGROUND OF THE INVENTION

A currently known breath-training device is comprised of a respiratory tube; a low-frequency mechanical air oscillation generator housing an oscillation chamber with an input channel, shaped as an upwardly extending saddle-shaped body of revolution ("saddle") containing a spherical ball and connected to a respiratory tube, and to an output channel that vents into the ambient atmosphere; and a tubular attachment communicating with the respiratory tube via an inhalation valve (RU 2147906 C1, A63B33/00, 2000). The main disadvantage of that device is difficulty of regulation of the resistance to the exhaled airflow. Currently, the resistance is regulated by the position of the spherical ball in the input channel of the oscillation chamber, which decreases the efficiency of the training process.

SUMMARY OF THE INVENTION

The present invention serves to increase the efficiency of the breath-training device by providing means of regulation of the resistance to the exhaled airflow.

Said device is comprised of a respiratory tube, a low-frequency mechanical air oscillation generator housing an oscillation chamber with an input channel, shaped as a "saddle" and containing a spherical ball, connected to the respiratory tube and venting into the ambient atmosphere, and a tubular attachment communicating with the respiratory tube via an inhalation valve. According to the invention, provided is the respiratory tube of the breath-training device with a jacket, in which the body of the low-frequency mechanical air oscillation generator is mounted with capability for rotation about the horizontal axis and a bypass chamber with an inhalation tube is formed. This inhalation tube contains an inhalation valve equipped with a tubular attachment. The output channel of the low-frequency mechanical air oscillation generator's oscillation chamber is equipped with an additional exhalation valve.

Besides, the case housing the low-frequency mechanical air oscillation generator is provided with a latch fixing a turned position.

The claimed connection of the respiratory tube to the jacket and fastening the tube in the case while it can rotate around the horizontal axis of the case of the low-frequency mechanical air oscillation generator allows one to change the position of the spherical ball in the output channel of the oscillating chamber, to adjust the breath training device to the resonance mode and, accordingly, to control the resistance to the flow of the exhaled air, therefore, increasing the efficiency of the training process.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
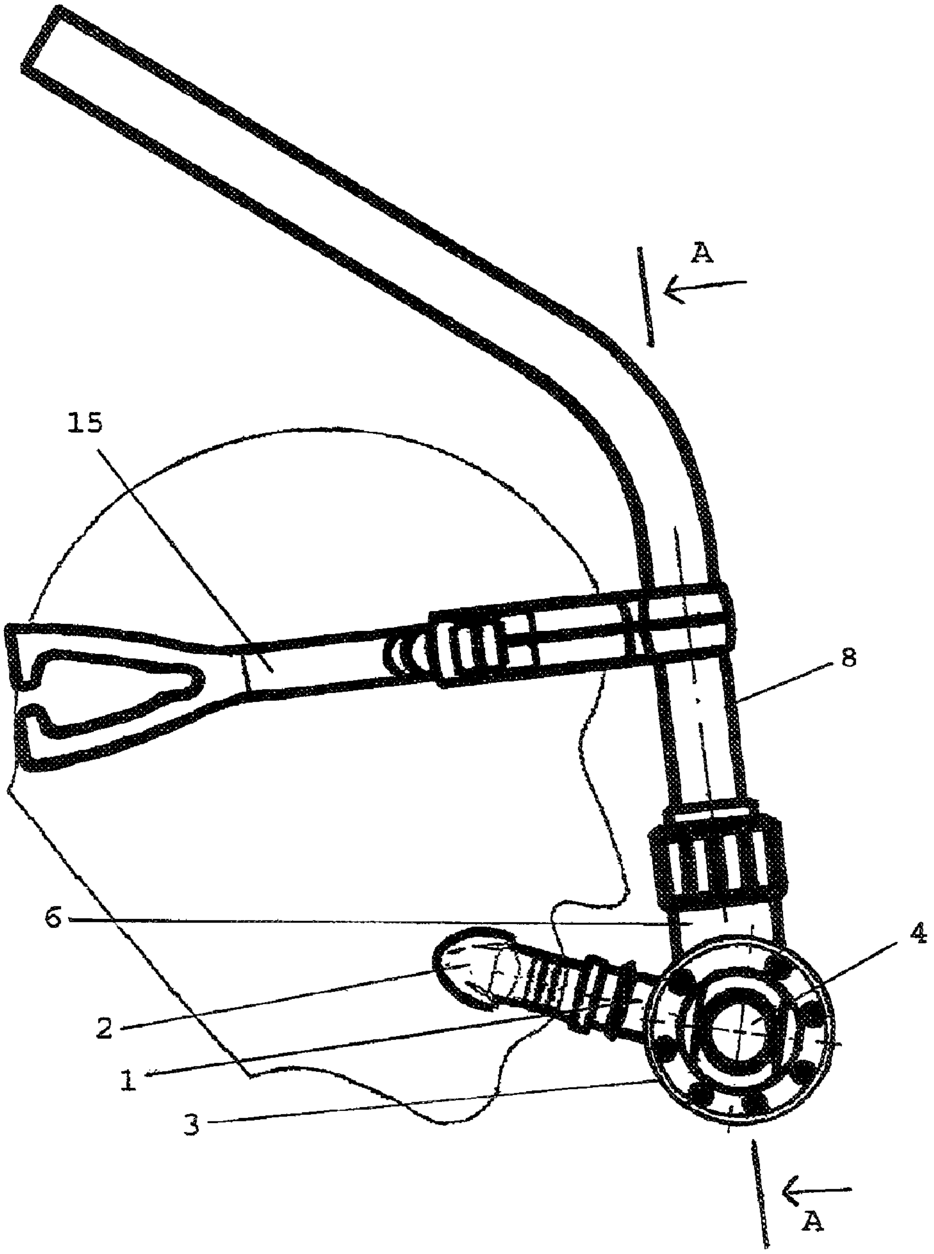
FIG. 1 presents the overall view of the breath-training device.
Figure 2:
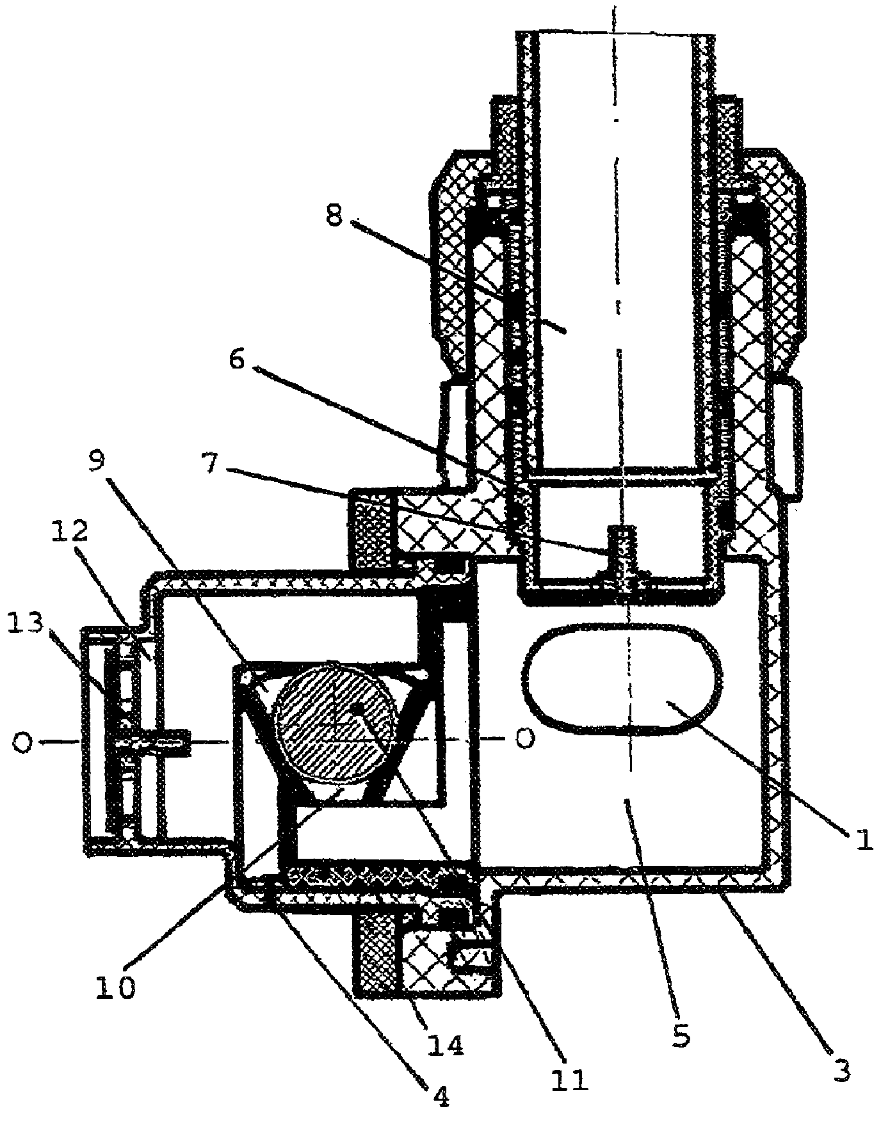
FIG. 2 presents a section along axis A-A as indicated on FIG. 1.

Breath-training device contains a respiratory tube (1) with a bite-board (2) connected to the jacket (3). The case (4) of the low-frequency mechanical air oscillation generator is mounted inside the jacket (3) with capability for rotation about the horizontal axis (O-O); also, bypass chamber (5) is formed, with an inhalation jet (6); the inhalation jet (6) is equipped with an inhalation valve (7) provided with a tubular attachment (8). The oscillation chamber (9) with its input channel (10) is housed inside the case (4) of the low-frequency mechanical air oscillation generator. The input channel (10) is shaped as an upwardly extending body of revolution ("saddle") containing a spherical ball (11). The output channel (12) of the oscillation chamber (10) contains the exhalation valve (13). In addition, the case (4) of the low-frequency mechanical air oscillation generator is equipped with latch (14) fixing its angle relative to the jacket (3). The device is also equipped with a fastener (head strap) (15) for user's convenience.

The breath-training device operates as follows: when the user inhales, inhalation valve (7) opens and air flows from the tubular attachment (8) through the inhalation jet (6) info the bypass chamber (5) (located inside the jacket (3)) and follows the respiratory tube (1) into the user's mouth. At this point, the exhalation valve (13) is closed and the spherical ball (11) rests in the "saddle" blocking the input channel (10) of the low-frequency mechanical air oscillation generator's oscillation chamber (9). When the user exhales, pressure of airflow closes the inhalation valve (7) blocking inhalation jet (6); the airflow from the bypass chamber (5) (located inside the jacket (3)) enters the oscillation chamber (9) of the low-frequency mechanical air oscillation generator via the input channel (10) displacing the spherical ball (11) from the "saddle" of the input channel (10); opening the exhalation valve (13) airflow vents into the ambient atmosphere through the output channel (12) while overcoming the resistance of the oscillation chamber (9) and exhalation valve (13).

As the spherical ball (11) interacts with the airflow inside the "saddle" of the input channel (10) of the oscillation chamber (9), it produces forced oscillations of low frequency, akin to those produced by a mechanical oscillation generator; these modulate the oscillation in the airflow exhaled, and, thus, the oscillation of the user's airways walls themselves, particularly, of the trachea. The position (upward displacement from resting position) of the spherical ball (11) at the moment of exhale is defined by the angle of inclination of the vertical axis of the oscillation chamber (9) relative to horizontal axis O-O and by instantaneous value of airflow pressure, controlled by the user's exhale. The angle of inclination depends on the relative position of the case (4) of the low-frequency mechanical air oscillation generator to the jacket (3).

The optimal efficiency of the proposed device is achieved by ascertainment of the mode of resonance. Mode (occurrence) of resonance is defined as maximal amplitude of oscillation (highest position) of the spherical ball (11), when the frequency of low-frequency oscillations of the ball (11) approaches that of user's tracheal walls. This causes a rapid increase in the amplitude of the forced oscillations of the exhaled airflow and, correspondingly, of the tracheal wall, which, in turn, stimulates operation of the smooth musculature of the lungs. The resulting bronchodilating effect leads to a more rapid adaptation to the physical strain under condition of cyclic exercise.

To adapt the breath-training device to the optimal mode of resonance, the position of the spherical ball (11) inside the output channel (10) of the oscillation chamber (9) can be adjusted by rotating of the case (4) of the low-frequency mechanical air oscillation generator inside the jacket (3), relative to the horizontal axis O-O and securing a chosen position with the latch (14).

While this invention has been particularly shown and described with references to preferred embodiments thereof, it will be understood by those skilled in the art that various changes in form and details may be made therein without departing from the scope of the invention encompassed by the appended claims.

What is claimed is:

1. A breath training device comprising:

a respiratory tube encased in a jacket;

a low-frequency mechanical generator of air oscillations placed inside the jacket, the low-frequency mechanical generator comprising a body fixed inside the jacket such that it is rotatable about a horizontal axis, a vibration chamber placed inside the body, the vibration chamber having an input channel and an output channel, and a spherical ball;

wherein the input channel is an upwardly expanding saddle-shaped body of revolution, wherein the spherical ball is placed inside the saddle-shaped body, wherein the input channel is associated with the respiratory tube, and wherein the output channel is associated with ambient environment via an exspiratory valve; and a bypass chamber inside the jacket comprising an inspiratory valve with a tubular attachment associated with the respiratory tube via the inspiratory valve.

2. A breath training device according to claim 1 wherein the body of the low-frequency mechanical generator of air oscillations further comprises a latching device for fixing the body in a revolved position.

* * * * *